(12) United States Patent
Iwao

(10) Patent No.: US 6,604,418 B2
(45) Date of Patent: Aug. 12, 2003

(54) LIQUID-LEVEL DETECTION METHOD AND DEVICE THEREOF

(75) Inventor: Toshikazu Iwao, Kyoto (JP)

(73) Assignee: Arkray, Inc., Kyoto (JP)

( * ) Notice: Subject to any disclaimer, the term of this patent is extended or adjusted under 35 U.S.C. 154(b) by 0 days.

(21) Appl. No.: 09/836,277

(22) Filed: Apr. 18, 2001

(65) Prior Publication Data

US 2001/0032505 A1 Oct. 25, 2001

(30) Foreign Application Priority Data

Apr. 19, 2000 (JP) .................................. 2000-117767

(51) Int. Cl.$^7$ ............................................. G01F 23/00
(52) U.S. Cl. ......................... 73/299; 73/202; 73/37.7; 73/303
(58) Field of Search ...................... 73/299, 202, 37.7, 73/303

(56) References Cited

FOREIGN PATENT DOCUMENTS

JP  2-196964 * 8/1990 .......... G01N/35/06

* cited by examiner

Primary Examiner—Daniel S. Larkin
Assistant Examiner—André Jackson
(74) Attorney, Agent, or Firm—Rader, Fishman & Grauer PLLC

(57) ABSTRACT

An ALC circuit is turned on (S1), a nozzle is shifted to a sampling position (S2), and after the ALC circuit has been turned off (S3), the nozzle is allowed to start discharging air from its tip (S4). While the nozzle is being lowered, the inner pressure of the nozzle is monitored (S5, S6), and upon detection of an increase in the pressure, the discharging process of air and the nozzle lowering process are stopped (S7), while the monitoring of the magnitude of the pressure is continued (S8). When the magnitude of the pressure is being maintained within a permissible range of the change for a predetermined time, it is judged that the tip of the nozzle has come into contact with the true liquid level, and after a suction operation of a sample (S9), the nozzle is raised (S10). When the magnitude of the pressure has dropped below the permissible range of the change within the predetermined time, it is judged that the tip of the nozzle has not come into contact with the true liquid level, the nozzle is again lowered (S11).

3 Claims, 6 Drawing Sheets

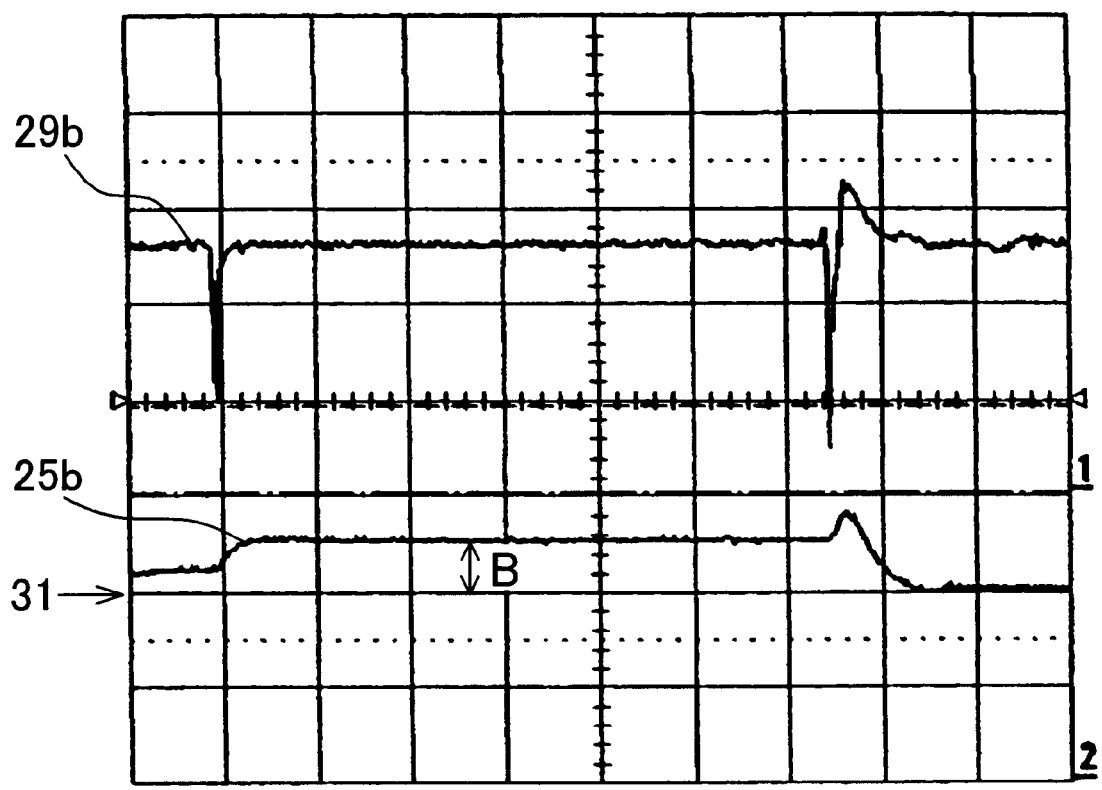

LIQUID-LEVEL DETECTION METHOD AND DEVICE THEREOF

BACKGROUND OF THE INVENTION

1. Field of the Invention

The present invention relates to a method and device for detecting a liquid level, and more specifically, concerns a liquid-level detection method and device, in which a nozzle is lowered toward a liquid level while a gas is being suctioned or discharged from a tip of the nozzle through a pipe by a pump so that, when the inner pressure of the pipe changes, it is judged that the tip of the nozzle has come into contact with the liquid level.

Such liquid-level detection method and device are applied to a biochemical automatic analyzer for measuring a sample such as blood or urine.

2. Description of the Prior Art

Liquid-level detection methods of this type have been disclosed in, for example, Japanese Unexamined Patent Application Nos. 196964/1990 (Hei 2-196964) and 243960/1990 (Hei 2-243960) gazettes.

The liquid-level detection method disclosed in the above-mentioned Japanese Unexamined Patent Application No. 196964/1990 (Hei 2-196964) is provided with the steps of preliminarily suctioning air into a nozzle chip; shifting the chip toward a position above a sample tube; lowering the chip toward a liquid level inside the sample tube while discharging air that has been suctioned; setting an inner pressure of an air hose (pipe) that has been obtained by a sampling process after a lapse of a predetermined period of time from the start of the lowering of the chip as a reference value; detecting a change in the inner pressure from the reference value that takes place when a suction inlet of the chip has come into contact with the liquid level and is closed; and making judgment that a tip of the nozzle has reached the liquid level when the change has been detected.

The liquid-level detection method disclosed by the above-mentioned Japanese Unexamined Patent Application No. 243960/1990 (Hei 2-243960) is provided with a pressure sensor for detecting a pressure of a flowing system (corresponding to the pipe) that allows a pump and a pipet (corresponding to the chip) to communicate with each other, and detects the liquid level from the pressure change inside the flowing system detected by the pressure sensor while the pipet is lowered with the pump being driven.

In these liquid-level detection methods, when the tip of the chip has come into contact with the liquid level, the air discharge from the tip of the chip is blocked by the liquid level with the result that the inner pressure of the pipe is raised; thus, it is judged that the tip position of the chip at this time corresponds to the liquid level position.

For example, in an automatic analyzer for measuring a sample such as blood or urine, it has been conventionally known that in an automatic injection, a slight difference in the amount of injection of a sample is greatly reflected in the measured value. Therefore, the depth of insertion of the chip is minimized by detecting the liquid level of a sample so that it is possible to reduce adhesion of the sample to the outer wall of the chip, and consequently to improve the precision in the amount of injection.

For example, in the case when the sample is a liquid such as blood and urine, bubbles and films can exist above the sample liquid level inside a container in which the sample is housed. When a liquid-level detecting process is carried out with such bubbles and films above the liquid level, the inner pressure of the pipe increases when the tip of the chip has come into contact with the bubbles and films, resulting in the control part making a judgment that the position of the tip of the chip at this time corresponds to the liquid level position, and starts the suction process, failing to carry out an accurate suction process for the sample.

SUMMARY OF THE INVENTION

The objective of the present invention is to provide a liquid-level detection method and device, which can carry out an accurate liquid level detection even when bubbles and films are located above the liquid level.

The liquid-level detection method in accordance with the present invention is provided with: a lowering step of lowering a nozzle toward a liquid level while a gas is being suctioned or discharged from the tip of the nozzle by a pump; a detection step of, upon detection of a change in the inner pressure of a pipe connected to the nozzle, stopping the suction process or discharging process of the pump and the lowering process of the nozzle; and a judging step of making a judgment that the tip of the nozzle has come into contact with the liquid level when a predetermined time has elapsed with the inner pressure in the pipe being maintained within a predetermined permissible range of the amount of change.

Here the term "nozzle" is used under the assumption that the nozzle includes the chip, in the case when a chip is attached to the tip of a nozzle.

The liquid-level detection device in accordance with the present invention is provided with: a pump for suctioning and discharging a gas so that a liquid is suctioned and discharged from a tip of a nozzle; a nozzle driving mechanism for raising and lowering the nozzle; a pressure sensor for measuring an inner pressure of a pipe connected to the nozzle; and a control part which controls the pump and the nozzle driving mechanism so as to lower the nozzle toward the liquid level while suctioning or discharging the gas from the tip of the nozzle, and to stop the operations of the pump and the nozzle driving mechanism upon detection of a change in the inner pressure of the pipe by the pressure sensor, and makes a judgment that the tip of the nozzle has come into contact with the liquid level when a predetermined time has elapsed with the output of the pressure sensor being maintained within a predetermined permissible range of the amount of change.

In the liquid-level detection method and device in accordance with the present invention, when the inner pressure of the pipe connected to the nozzle changes, the suction process or discharging process of the pump and the lowering operation of the nozzle are discontinued, and a judgment is made as to whether or not a predetermined time has elapsed with the inner pressure in the pipe being maintained within a predetermined permissible range of the amount of change. When the change in the inner pressure of the pipe is caused by bubbles and films located above the liquid level, the pressure change is a temporary phenomenon, and when the suction process or discharging process of the gas from the tip of the nozzle is discontinued, the inner pressure of the pipe varies to approach the pressure open to atmosphere as time elapses. In contrast, in the case when a change in the inner pressure of the pipe is caused by the liquid level, the inner pressure of the pipe barely changes even when time has elapsed after the stoppage of the suction or discharge of the gas from the nozzle tip.

In this manner, in the liquid-level detection method and device in accordance with the present invention, upon detection of a change in the inner pressure of the pipe, the suction or discharging process of the pump and the lowering operation of the nozzle is discontinued, and the following pressure variations are monitored so that it is judged whether the change in the inner pressure of the pipe is caused by the liquid level or bubbles and films; thus, it is possible to reduce the probability of misdetection due to bubbles and films, consequently to accurately detect the liquid level.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 9 is a drawing that shows an output waveform of a pressure signal AMP 25 and an output waveform of a differential signal AMP 29 at the time of the liquid level being detected, with 70% ethanol being used as a sample.

DESCRIPTION OF THE PREFERRED EMBODIMENTS

With respect to the liquid level detection method of the present invention, in the detection step, it is preferable to make a judgment as to the change in the inner pressure based upon comparison between the differential signal of the inner pressure and a threshold value, and in the judging step, it is preferable to make a judgment based upon the pressure signal itself from the inner pressure. As a result, it is possible to quickly detect the clogging of the tip of the nozzle, and also to accurately monitor the variations in the inner pressure.

In the liquid-level detection device of the present invention, the control part is preferably provided with an ALC (Auto Level Control) circuit that sets the output of the pressure sensor at the time when the nozzle is open to atmosphere to a center of the input range of an AD (analog-to-digital) converter of the control part.

In the case of a device which carries out sample injection in fine amount, for example, approximately 10 micro-liters, the inner diameter of a nozzle and a pipe, such as a tube, between the nozzle and the pump is very small, and the change in the inner pressure of the pipe that takes place when the tip of the nozzle comes into contact with the liquid level is also small; therefore, the output of the pressure sensor needs to be amplified with a great gain. However, when the amplification is made with a great gain, problems arise in which the dynamic range is exceeded or it is not possible to maintain a constant value, caused by changes in offsets in the pressure sensor and the amplifier due to temperature changes, or influences of deviations due to aged deterioration. Therefore, the ALC circuit is used to set the output of the pressure sensor when the nozzle is open to atmosphere, to a center of the input range of an AD converter, and immediately before the start of the liquid level detection, the ALC circuit is turned off so that an output in accordance with the inner pressure of the pipe can be monitored by using a proper range.

The control part is preferably provided with a differential circuit for outputting the rate of change in the output of the pressure sensor, and it is preferable to detect the change in the inner pressure of the pipe based upon the change of the output from the differential circuit In addition to the detection in a change in the inner pressure of the pipe based upon the change in the output in accordance with the magnitude of the pressure, the change in the inner pressure is detected based upon the rate of change in the output of the pressure sensor; thus, it becomes possible to quickly detect the change in the inner pressure of the pipe.

The pressure sensor is preferably placed in the vicinity of the tip of the nozzle. Consequently, it becomes possible to suppress variations in the output of the pressure sensor due to changes in the inner pressure of the nozzle at the time of the starting of the suction or discharging operation.

Figure 1:
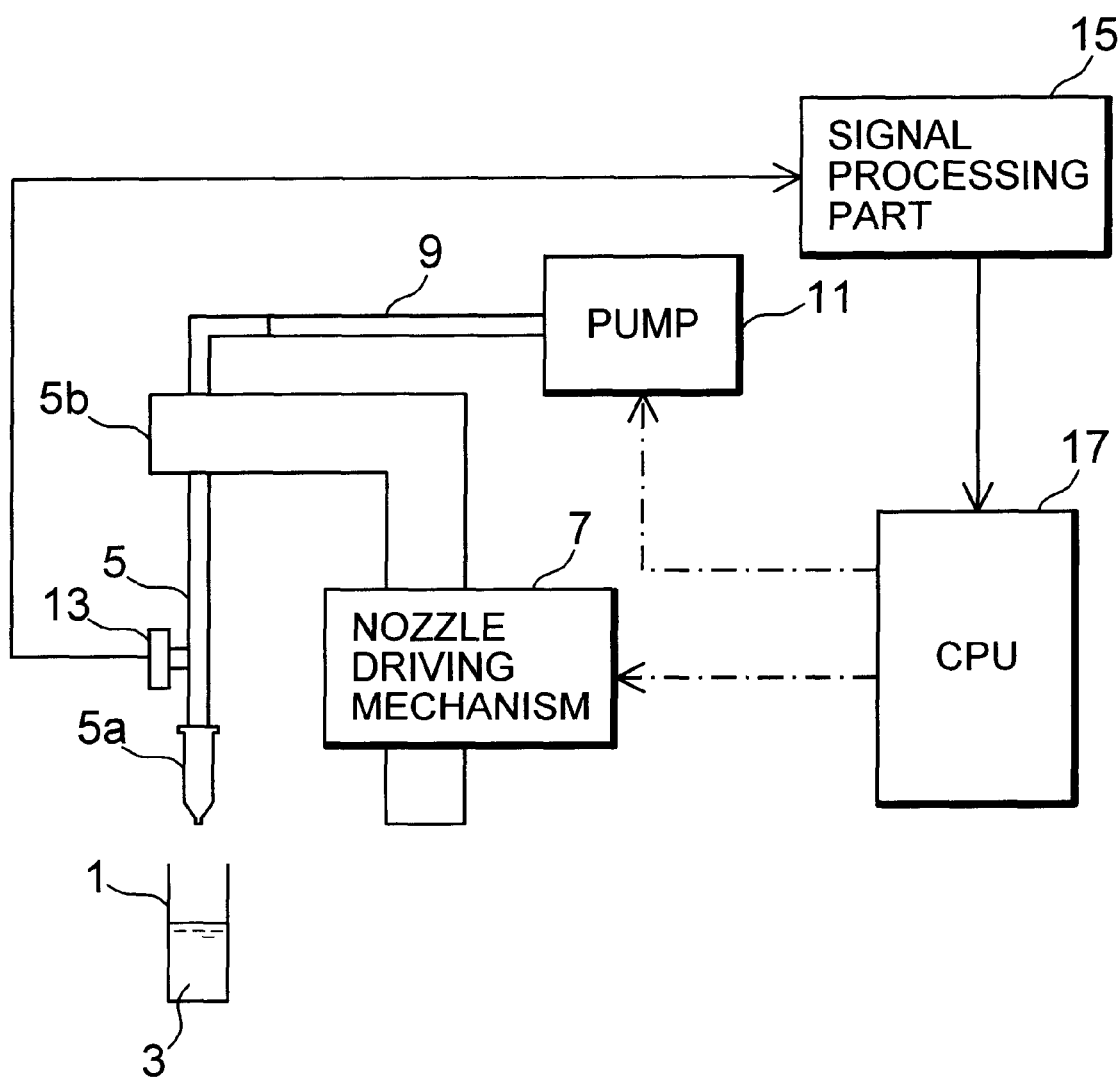
FIG. 1 is a schematic drawing that shows the construction of an extraction device in accordance with one embodiment of the present invention.
Figure 2:
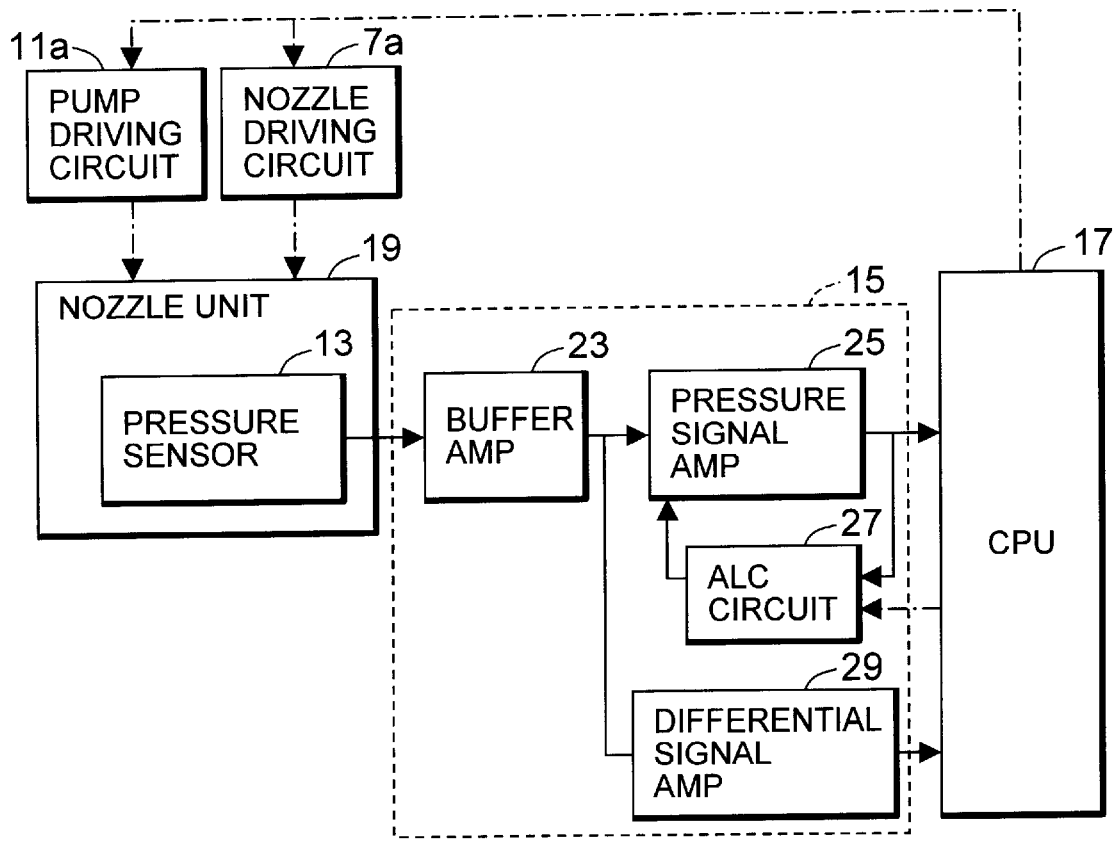
FIG. 2 is a block diagram that shows a control system of the embodiment.

FIG. 1 is a schematic drawing that shows a construction of an extraction device in accordance with one embodiment FIG. 2 is a block diagram of the embodiment.

A disposable chip 5a for taking one portion of a sample 3 housed in a container 1 in its inner side is detachably attached to one end of a nozzle 5. The nozzle 5 is placed on an arm 5b, and raised and lowered together with the arm 5b by a nozzle driving mechanism 7. The other end of the nozzle 5 is connected to a pump 11 through a tube 9.

A pressure sensor 13 for measuring the inner pressure of piping that contains the chip 5a, the nozzle 5, the tube 9 and the pump 11 is attached to the nozzle 5. The pressure sensor 13 is placed in the vicinity of the tip of the nozzle 5. For this reason, it is possible to suppress variations in the output of the pressure sensor 13 due to changes in the inner pressure of the nozzle 5 at the time of the starting of the suction or discharging operation of the pump 11. With respect to the pressure sensor 13, a sensor constituted by piezo-elements is used.

FIG. 2 shows a controlling system of the present embodiment, and the nozzle 5, the chip 5a, the arm 5b, the nozzle driving mechanism 7, the tube 9 and the pump 11 of FIG. 1 are included in a nozzle unit 19. A nozzle driving circuit 7a for controlling the operation of the nozzle driving mechanism 7 and a pump driving circuit 11a for controlling the operation of the pump 11 are electrically connected to the nozzle unit 19. The nozzle driving circuit 7a and the pump driving circuit 11a are electrically connected to a CPU 17, and the driving operations thereof are controlled by the CPU 17.

The pressure sensor 13 of the nozzle unit 19 is electrically connected to a signal processing part 15. The signal processing part 15 is provided with a buffer amplifier (hereinafter, an amplifier is referred to as AMP) 23, a pressure signal AMP 25, an ALC circuit 27 and a differential signal AMP 29. The differential circuit constituting the present invention is actualized by the differential signal AMP 29.

Figure 3:
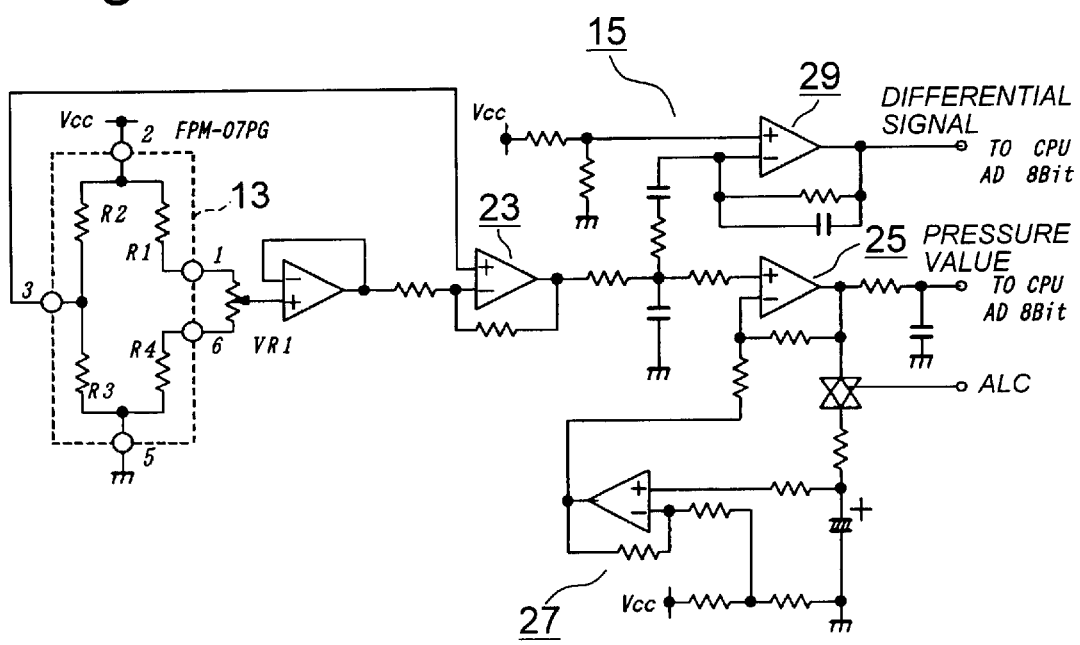
FIG. 3 is a circuit diagram that shows one example of a pressure sensor and a signal processing part.

FIG. 3 is a circuit diagram that shows one example of the pressure sensor 13 and the signal processing part 15.

The output of the pressure sensor 13 is inputted to the buffer AMP 23. The buffer AMP 23 amplifies the output of the pressure sensor 13 to, for example, 100 times, and outputs this to the pressure signal AMP 25 and the differential signal AMP 29. The pressure signal AMP 25 further amplifies the output amplified by the buffer AMP 23 to approximately 50 times, and outputs this to the CPU 17. The ALC circuit 27 is connected to the input side of the pressure signal AMP 25, and its on/off switching is controlled by the CPU 17; thus, when it is turned on, it functions to set the output of the pressure signal AMP 25 to a center of the input range of the AD converter (not shown) through which the output of the pressure AMP 25 directed to the CPU 17. The differential signal AMP 29 outputs the rate of change in the output amplified by the buffer AMP 23 to the CPU 17.

Figure 4:
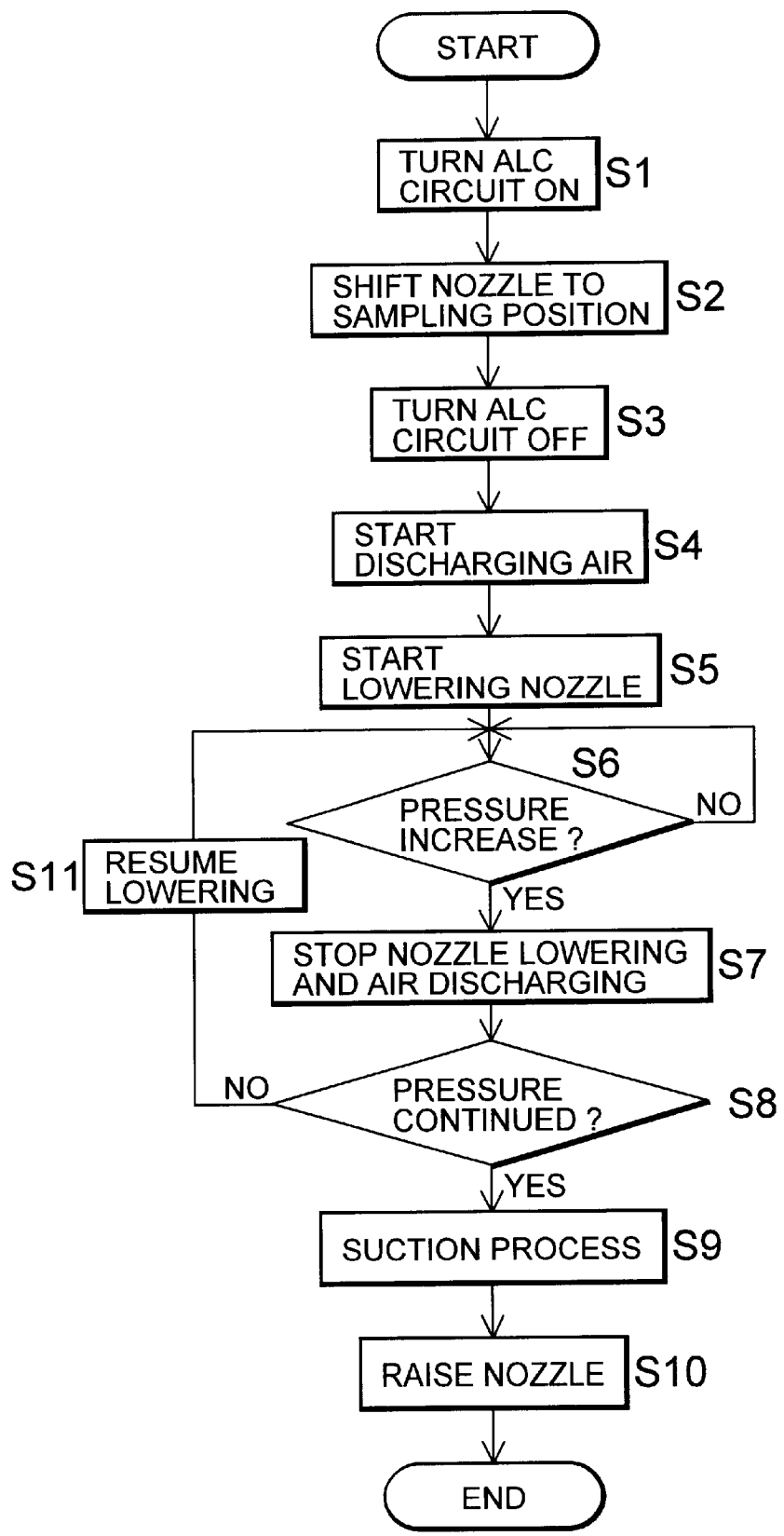
FIG. 4 is a flow chart that shows the liquid level detection operation and the sample suction operation of the embodiment.

FIG. 4 is a flow chart that shows the liquid level detection operation and the sample suction operation of the present embodiment Referring to FIGS. 1 to 4, an explanation will be given of these operations.

The ALC circuit 27 is turned on by the CPU 17 so that the output of the pressure signal AMP 25 is maintained at the center of the input range of the AD converter through which it is directed to the CPU 17 (step S1). The CPU 17 controls the nozzle driving circuit 7a so that the nozzle driving mechanism 7 allows the nozzle 5 and the chip 5a to a sampling position above the container 1 (step S2).

After the ALC circuit 27 has been turned off by the CPU 17 (step S3), the pump driving circuit 11a is controlled so that the pump 11 is operated to carry out a discharging operation, thereby starting to discharge air from the tip of the chip 5a through the tube 9 and the nozzle 5 (step S4).

While air is being discharged from the tip of the chip 5a, the CPU 17 controls the nozzle driving circuit 7a so that the nozzle driving mechanism 7 lowers the nozzle 5 and the chip 5a toward the liquid level of a sample 3 (step S5). At this time, the CPU 17 monitors the output of the pressure signal AMP 25 and the output of the differential signal AMP 29 (step S6).

Figure 5:
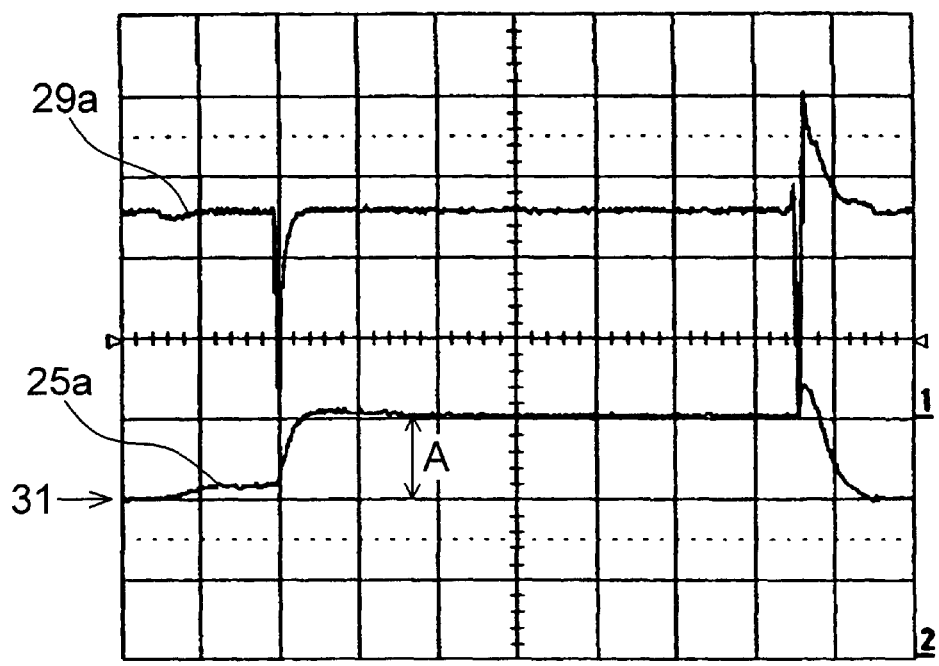
FIG. 5 is a drawing that shows an output waveform of a pressure signal AMP and an output waveform of a differential signal AMP at the time of the tip of a chip coming into contact with the true liquid level, with blood being used as a sample.
Figure 6:
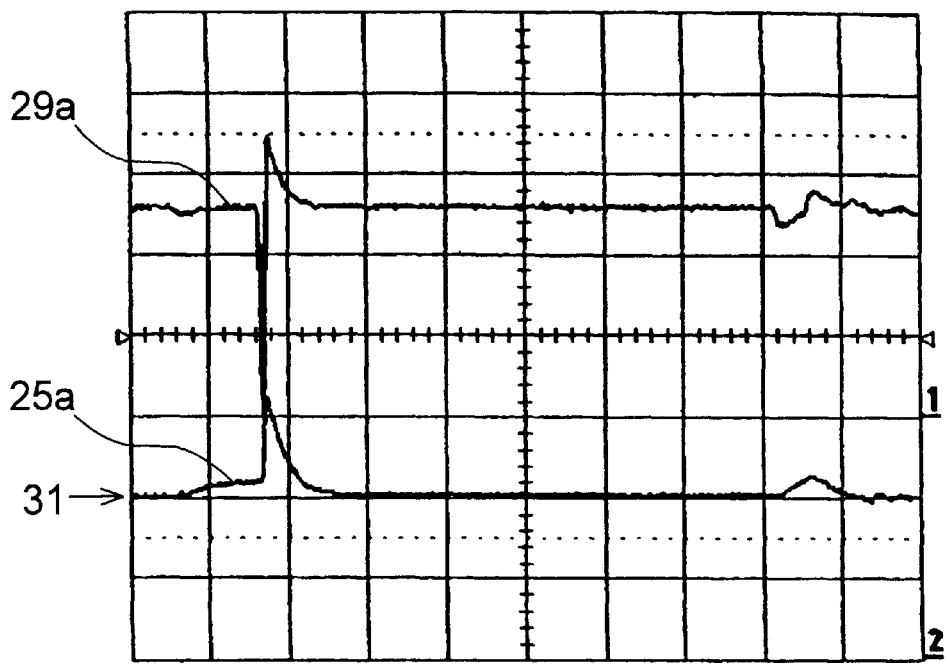
FIG. 6 is a drawing that shows an output waveform of a pressure signal AMP and an output waveform of a differential signal AMP at the time of the tip of a chip coming into contact with bubbles, with blood being used as a sample.
Figure 7:
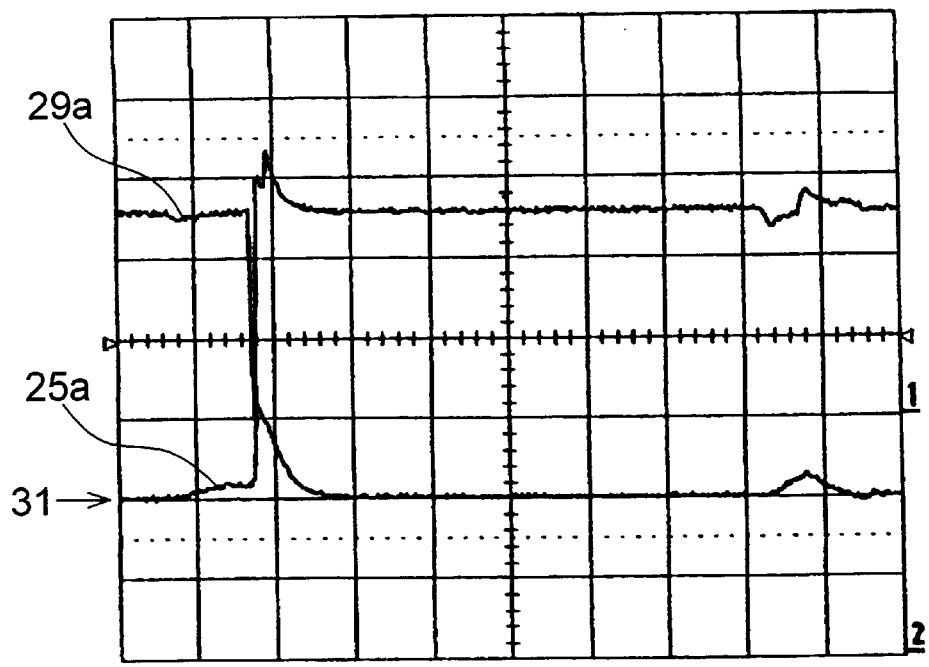
FIG. 7 is a drawing that shows an output waveform of a pressure signal AMP and an output waveform of a differential signal AMP at the time of the tip of a chip coming into contact with films, with blood being used as a sample.
Figure 8:
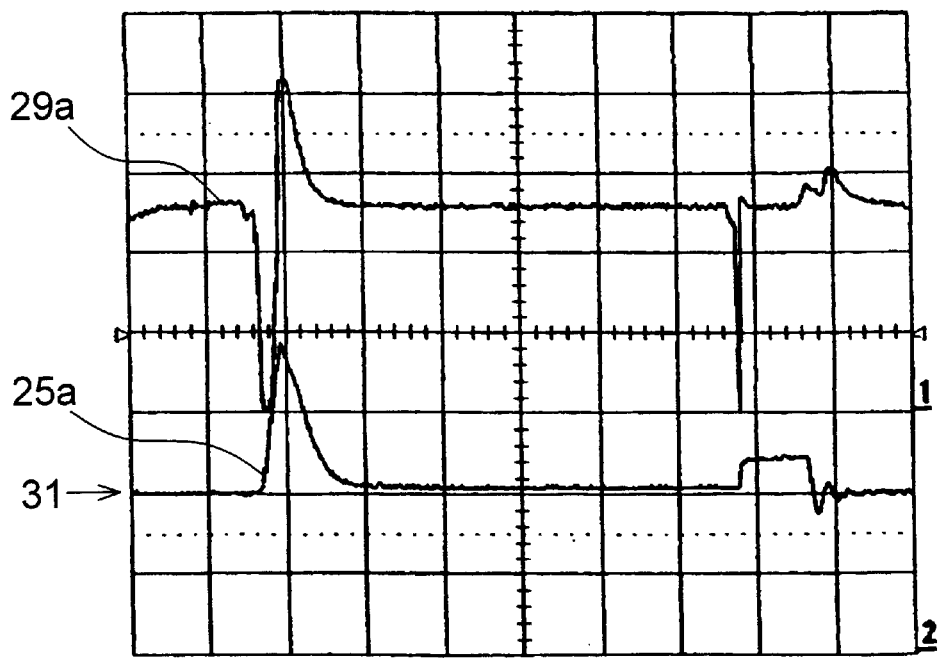
FIG. 8 is a drawing that shows an output waveform of a pressure signal AMP and an output waveform of a differential signal AMP at the time of the tip of a chip being clogged due to liquid drops inside the tip, with blood being used as a sample.

FIGS. 5 to 8 are drawings that show the output waveform of the pressure signal AMP 25 and the output waveform of the differential signal AMP 29 at the time of blood being used as a sample; FIG. 5 shows those derived from the true liquid level; FIG. 6 shows those derived from bubbles; FIG. 7 shows those derived from films; and FIG. 8 shows those derived from liquid drops inside the chip. The axis of ordinate represents the signal intensity, and the axis of abscissa represents time.

In FIGS. 5 to 8, reference number 25a represents the output waveform of the pressure signal AMP 25 (hereinafter, referred to as "pressure signal waveform"), and although the ALC circuit 27 is off, the waveform starts from a center level 31 due to the function of the ALC circuit 27 prior to the off state. Reference number 29a represents the output waveform (hereinafter, referred to as "differential signal waveform") of the differential signal AMP 29.

Referring to FIGS. 5 to 8, the explanation is further given on the operation of the present embodiment. When the tip of the chip 5a is clogged by coming into contact with the liquid level, bubbles or films of the sample 3, or when the tip of the chip 5a is clogged by liquid drops within the chip, the inner pressure of the nozzle 5 increases, resulting in a fall in the differential signal waveform 29a (the differential signal AMP 29 is connected so as to provide such a polarity), as well as resulting in a rise in the pressure signal waveform 25a at the same time. When the fall of the differential signal waveform 29a goes below a threshold value, the CPU 17 controls the nozzle driving circuit 7a so that the operation of the nozzle driving mechanism 7 is stopped so that the lowering operations of the nozzle 5 and the chip 5a are stopped, and also controls the pump driving circuit 11a so that the operation of the pump 11 is stopped (step S7), thereby continuing the monitoring of the pressure signal waveform 25a (step S8).

In the case when the tip of the chip 5a has come into contact with the true liquid level, the inner pressure of the nozzle 5 is maintained virtually at a constant level. As illustrated in FIG. 5, the differential signal waveform 29a is allowed to return to the output prior to the fall, while the output of the pressure signal waveform 25a is maintained in the raised state. When, after the changes in the pressure signal waveform 25a and the differential signal waveform 29a, the raised state of the pressure signal waveform 25a has continued for a predetermined judging time while being maintained within a permissible range of the change, the CPU 17 makes a judgment that the tip of the chip 5a has come into contact with the true liquid level. The permissible range of the change and the judging time may be properly set. For example, the permissible range of the change is set to 50%, and the judging time is set to 6 seconds. Then, the tip of the chip 5a is inserted from the liquid level to a minimum depth that allows it to positively suction a predetermined amount of the sample 3, and the pump 11 is operated to suction the sample 3 into the chip 5a (step S9). After the suction operation of the sample 3, the nozzle 5 and the chip 5a are raised (step S10).

In contrast, when the pressure rise at the step S6 is derived from bubbles (see FIG. 6), films (see FIG. 7) or liquid drops within the chip (see FIG. 8), the inner pressure of the nozzle 5, once raised, returns to the state that is open to atmosphere, as time elapses. Consequently, the raised pressure signal waveform 25a approaches the center level 31. When, after the changes in the pressure signal waveform 25a and the differential signal waveform 29a, the pressure signal waveform 25a has fluctuated beyond the permissible range of the change, within 6 seconds of the judging time, the CPU 17 makes a judgment that the tip of the chip 5a has not come into contact with the true liquid level, and resumes to lower the nozzle 5 and the chip 5a (step S11).

In this manner, in accordance with the present invention, it is possible to avoid the probability of misdetection of the liquid level due to bubbles, films, or liquid drops within the chip, and consequently to detect the true liquid level. Moreover, in the case when only small bubbles exist on the liquid level, since these small bubbles are wiped out by air discharged from the tip of the nozzle 5a, it is possible to carry out an appropriate detection on the liquid level.

Moreover, it is preferable to provide the following operation: in the case when a variation of the pressure signal waveform 25a or the differential signal waveform 29a has been detected at a position higher than the expected liquid level position, this is recognized as a misdetection due to external noise or liquid drops within the chip, and the same operation is resumed.

Furthermore, in accordance with the present invention, it is also possible to make a judgment as to a difference in the viscosity of a sample. FIG. 9 is a drawing that shows the output waveform of the pressure signal AMP 25 and the output waveform of the differential signal AMP 29 at the time when the true liquid level is detected with 70% ethanol being used as the sample 3. The axis of ordinate represents the signal intensity, and the axis of abscissa represents time. Reference number 25b represents the pressure signal waveform, 29b represents the differential signal waveform, and 31 represents the center level. The signal intensity of FIG. 9 is a measured value in the case when the same gain as FIG. 5 is used.

In comparison with cases of blood being used as the sample 3 (see FIG. 5) and when 70% ethanol is used (see FIG. 9), in a state where the pressure signal waveform 25a, 25b has a rise upon contact of the tip of the chip with the liquid level of the blood or the 70% ethanol, an output intensity value A from the center level 31 of the pressure signal waveform 25a at the time of detection of the blood liquid level is greater than an output intensity value B from the center level 31 of the pressure signal waveform 25b at the time of detection of the 70% ethanol. In other words, in the state where the pressure signal waveform rises, the output intensity value in response to the magnitude of the viscosity of the sample is provided. Thus, it is possible to make ajudgment as to a difference in the viscosity in the sample.

In the above-mentioned extraction device, the chip is detachably attached to the tip of the nozzle, but, the present invention is not intended to be limited by this arrangement and may be applied to any extraction device in which the sample is suctioned and discharged into the nozzle without using the chip.

As illustrated in FIGS. 5 to 9, in the above-mentioned embodiment, the polarity of the amplifier is determined so that the rise of the inner pressure of the pipe is indicated in an upward extending manner and the increase of the rate of change in the inner pressure thereof is indicated in a downward extending manner. However, the present invention is not intended to be limited by this arrangement, and any polarity may be used with respect to the amplifier.

Moreover, in the above-mentioned embodiment, the nozzle is lowered while air is being discharged from the tip of the chip so that the increase in the inner pressure of the pipe is monitored. However, the present invention is not intended to be limited by this arrangement, and the nozzle may be lowered while air is being suctioned from the tip of the chip so that the decrease in the inner pressure of the pipe is monitored.

Although the present invention has been described and illustrated in detail, it is clearly understood that the same is by way of illustration and example only and is not to be taken by way of limitation as the spirit and scope of the present invention are limited only by the terms of the appended claims.

What is claimed is:

1. A liquid-level detection device comprising:

a pump for suctioning and discharging a gas so that a liquid is suctioned and discharged from a tip of a nozzle;

a nozzle driving mechanism for raising and lowering the nozzle;

a pressure sensor for measuring an inner pressure of a pipe connected to the nozzle; and a control part which controls the pump and the nozzle driving mechanism so as to lower the nozzle toward the liquid level while suctioning or discharging the gas from the tip of the nozzle, and to stop the operations of the pump and the nozzle driving mechanism upon detection of a change in the inner pressure of the pipe by the pressure sensor, and makes judgment that the tip of the nozzle has come into contact with the liquid level when a predetermined time has elapsed with the output of the pressure sensor being maintained within a predetermined permissible range of the amount of change, the control part including an ALC circuit that sets the output of the pressure sensor at the time when the nozzle is open to atmosperic pressure to a center of an input range of an AD converter of the control part.

2. The liquid-level detection device according to claim 1, wherein the control part further comprises a differential circuit that outputs a rate of change in the output of the pressure sensor so that a change in the inner pressure of the pipe is detected based upon the change in the output of the differential circuit.

3. The liquid-level detection device according to claim 1, wherein the pressure sensor is placed in the vicinity of the tip of the nozzle.

* * * * *